(12) United States Patent
Babin

(10) Patent No.: US 9,244,002 B1
(45) Date of Patent: Jan. 26, 2016

(54) OPTICAL METHOD AND SYSTEM FOR MEASURING AN ENVIRONMENTAL PARAMETER

(71) Applicant: INSTITUT NATIONAL D'OPTIQUE, Quebec (CA)

(72) Inventor: Francois Babin, Quebec (CA)

(73) Assignee: INSTITUT NATIONAL D'OPTIQUE, Québec, Quebec (CA)

( * ) Notice: Subject to any disclaimer, the term of this patent is extended or adjusted under 35 U.S.C. 154(b) by 0 days.

(21) Appl. No.: 14/449,511

(22) Filed: Aug. 1, 2014

(51) Int. Cl.
*G01N 21/00* (2006.01)
*G01N 21/27* (2006.01)
*G01N 21/25* (2006.01)

(52) U.S. Cl.
CPC ............ *G01N 21/274* (2013.01); *G01N 21/255* (2013.01); *G01N 2201/0612* (2013.01); *G01N 2201/082* (2013.01); *G01N 2201/0826* (2013.01)

(58) Field of Classification Search
CPC ............ G02F 1/13318; G01B 9/02014; G01B 9/02091; G01D 5/35335; G01D 5/35348; G01D 5/35383; G01L 1/243; G01L 1/247; G01N 2021/1793; G01N 2021/653; G01N 2021/655; G01N 21/65
See application file for complete search history.

(56) References Cited

U.S. PATENT DOCUMENTS 5,148,303 A * 9/1992 Biard .............. G01D 5/268
250/227.21
5,589,937 A * 12/1996 Brininstool ............ G01L 1/243
250/227.14
2002/0063866 A1 * 5/2002 Kersey ............... G01D 5/35383
356/478
2012/0147381 A1 6/2012 Leblanc et al.
2013/0062508 A1 * 3/2013 Kanter ................ H03M 1/1265
250/214 DC

FOREIGN PATENT DOCUMENTS

EP 0306227 B1 3/1989

OTHER PUBLICATIONS

B. J.-C. Deboux et al., A robust and miniature optical fibre pH sensor based on methylene blue dye adsorption, Proceeding of the SPIE, 1995, pp. 167-176, vol. 2542, Liverpool John Moores University, Liverpool, United Kingdom.
K. T. V. Grattan et al., Dual Wavelength Optical Fibre Sensor for pH Measurement, Biosensors, 1987/1988, p. 17-25, vol. 3, School of Electrical Engineering and Applied Physics, London, United Kingdom.

* cited by examiner

*Primary Examiner* — Michael P Stafira
(74) *Attorney, Agent, or Firm* — Fasken Martineau DuMoulin

(57) ABSTRACT

An optical system for sensing an environmental parameter, comprising: a pulse generator for generating a first pulse having a first wavelength and a second pulse having a second wavelength; a pulse splitter for splitting each one of the first and second pulse into a sensing pulse and a reference pulse; a sensing arm for receiving the sensing pulses therefrom and comprising a spectro-ratiometric sensor; a reference arm for receiving the reference pulses; a time delay line for delaying a relative propagation of the sensing pulses and the reference pulses; a light detector for measuring an optical energy of the sensing pulse and the reference pulse, for the first and second wavelengths; and at least one optical link for optically connecting the pulse generator to the pulse splitter, and the sensing and reference arms to the light detector.

20 Claims, 4 Drawing Sheets

OPTICAL METHOD AND SYSTEM FOR MEASURING AN ENVIRONMENTAL PARAMETER

CROSS-REFERENCE TO RELATED APPLICATIONS

This is the first application filed for the present invention.

TECHNICAL FIELD

The present invention relates to the field of optical measurement methods and systems, and more particularly to optical methods and systems using spectro-ratiometric sensors.

BACKGROUND

In various industries, point sensors are installed at various intervals along optical fibers that span long distances, e.g. from hundreds of meters to tens of kilometers. One type of sensor measures environmental parameters through the change in the spectral optical loss of the sensor. These sensors usually work at a number of different wavelengths, often tens to one or two hundred nanometers apart. Spectral loss, i.e. optical losses that vary with wavelength, and spectral loss stability in the fiber link then become important factors. In order to measure spectral loss in point sensors installed along optical fibers, often of great lengths, time evolution techniques such as fluorescence lifetime technique or ring down spectroscopy are usually used. These techniques can be time-consuming or require low-dispersion fibers which are inadequate in coupling thereto several sensors.

Therefore, there is a need for an improved optical sensing method and system.

SUMMARY

According to a first broad aspect, there is provided an optical system for sensing an environmental parameter, comprising: an optical pulse generator for generating a first pulse having a first wavelength and a second pulse having a second and different wavelength; a pulse splitter for splitting each one of the first and second pulse into a sensing pulse and a reference pulse; a sensing arm connected to the pulse splitter for receiving the sensing pulses therefrom, the sensing arm comprising a spectro-ratiometric sensor for sensing the environmental parameter; a reference arm connected to the pulse splitter for receiving the reference pulses therefrom; a time delay line contained in one of the sensing arm and the reference arm, the time delay line for delaying a propagation of one of the sensing pulses and the reference pulses relative to a propagation of another one of the sensing pulses and the reference pulses; a light detector for detecting the sensing pulse and the reference pulse and measuring an optical energy of the sensing pulse and the reference pulse, for the first and second wavelengths; and at least one optical link for optically connecting the pulse generator to the pulse splitter, and the sensing and reference arms to the light detector.

In one embodiment, the light detector comprises a photon counting detector.

In one embodiment, the photon counting detector comprises a gated photon counting detector.

In one embodiment, the at least one optical link comprises a single optical link In another embodiment, the at least one optical link comprises a first optical link for optically connecting the pulse generator to the pulse splitter, and a second optical link for optically connecting the sensing and reference arms to the light detector.

In one embodiment, the sensing and reference arms each further comprise a light reflector for reflecting the sensing pulses and the reference pulses, respectively.

In one embodiment, the at least one optical link comprises at least one optical fiber.

In one embodiment, the at least one optical fiber comprises at least one multimode fiber.

In one embodiment, the system further comprises a processor for determining a value of the environmental parameter using the measured optical energy for the sensing and reference pulses.

In one embodiment, the spectro-ratiometric sensor comprises an optical fiber-based optode comprising a sensing membrane, the sensing membrane comprising a chemical indicator causing a variation of the optical absorption as a function of the environmental parameter.

According to a second broad aspect, there is provided an optical system for sensing an environmental parameter, comprising: an optical pulse generator for generating a first pulse having a first wavelength and a second pulse having a second and different wavelength; a plurality of sensing units for sensing the environmental parameter, each comprising: a pulse splitter for splitting each one of the first and second pulse into a sensing pulse and a reference pulse; a sensing arm connected to the pulse splitter for receiving the sensing pulse therefrom, the sensing arm comprising a spectro-ratiometric sensor for sensing the environmental parameter; a reference arm connected to the pulse splitter for receiving the reference pulse therefrom; and a time delay line contained in one of the sensing arm and the reference arm, the time delay line for delaying a propagation of one of the sensing pulse and the reference pulse relative to a propagation of another one of the sensing pulse and the reference pulse; a light detector for detecting the sensing pulse and the reference pulse from each sensing unit and measuring an optical energy of the sensing pulse and the reference pulse from each sensing unit, for the first and second wavelengths; and at least one optical link for optically connecting the pulse generator to the pulse splitter, and the sensing and reference arms to the light detector.

According to another broad aspect, there is provided a method for remotely sensing an environmental parameter, comprising: generating a first pulse having a first wavelength and a second pulse having a second and different wavelength; propagating the first and second pulses along at least one optical link; splitting each one of the first and second pulse into a sensing pulse and a reference pulse; propagating the sensing pulses in a sensing arm, the sensing arm comprising an spectro-ratiometric sensor, thereby sensing the environmental parameter; propagating the reference pulses in a reference arm; delaying a propagation of one of the sensing pulses and the reference pulses relative to a propagation of another one of the sensing pulses and the reference pulses; propagating the sensing pulses and the reference pulses in the at least one optical link; and measuring an optical energy of the sensing pulse and the reference pulse, for each one of the first and second wavelengths.

In one embodiment, the step of propagating the first and second pulses along at least one optical link comprises propagating the first and second pulses along a first optical link, and the step of propagating the sensing pulses and the reference pulses in the at least one optical link comprises propagating the sensing pulses and the reference pulses in a second and different optical link.

In another embodiment, the step of propagating the first and second pulses along at least one optical link comprises propagating the first and second pulses along a single optical link, and the step of propagating the sensing pulses and the reference pulses in the at least one optical link comprises propagating the sensing pulses and the reference pulses in the single optical link.

In one embodiment, the step of propagating the first and second pulses along at least one optical link comprises propagating the first and second pulses along at least one optical fiber.

In one embodiment, the at least one optical fiber comprises at least one multimode fiber.

In one embodiment, the method further comprises a step of determining a value of the environmental parameter using the measured optical energy for the sensing and reference pulses.

In one embodiment, the step of propagating the sensing pulses in a sensing arm comprises reflecting the sensing pulses at an end of the sensing arm, and said propagating the reference pulses in a reference arm comprises reflecting the reference pulses at an end of the reference arm.

In one embodiment, the step of measuring an optical energy comprises counting a number of photons for each one of the sensing pulse and the reference pulse, for each one of the first and second wavelengths.

In one embodiment, the spectro-ratiometric sensor comprises an optical fiber-based optode comprising a sensing membrane, the sensing membrane comprising a chemical indicator causing a variation of the optical absorption as a function of the environmental parameter.

BRIEF DESCRIPTION OF THE DRAWINGS

Further features and advantages of the present invention will become apparent from the following detailed description, taken in combination with the appended drawings, in which.

It will be noted that throughout the appended drawings, like features are identified by like reference numerals.

DETAILED DESCRIPTION

Figure 1:
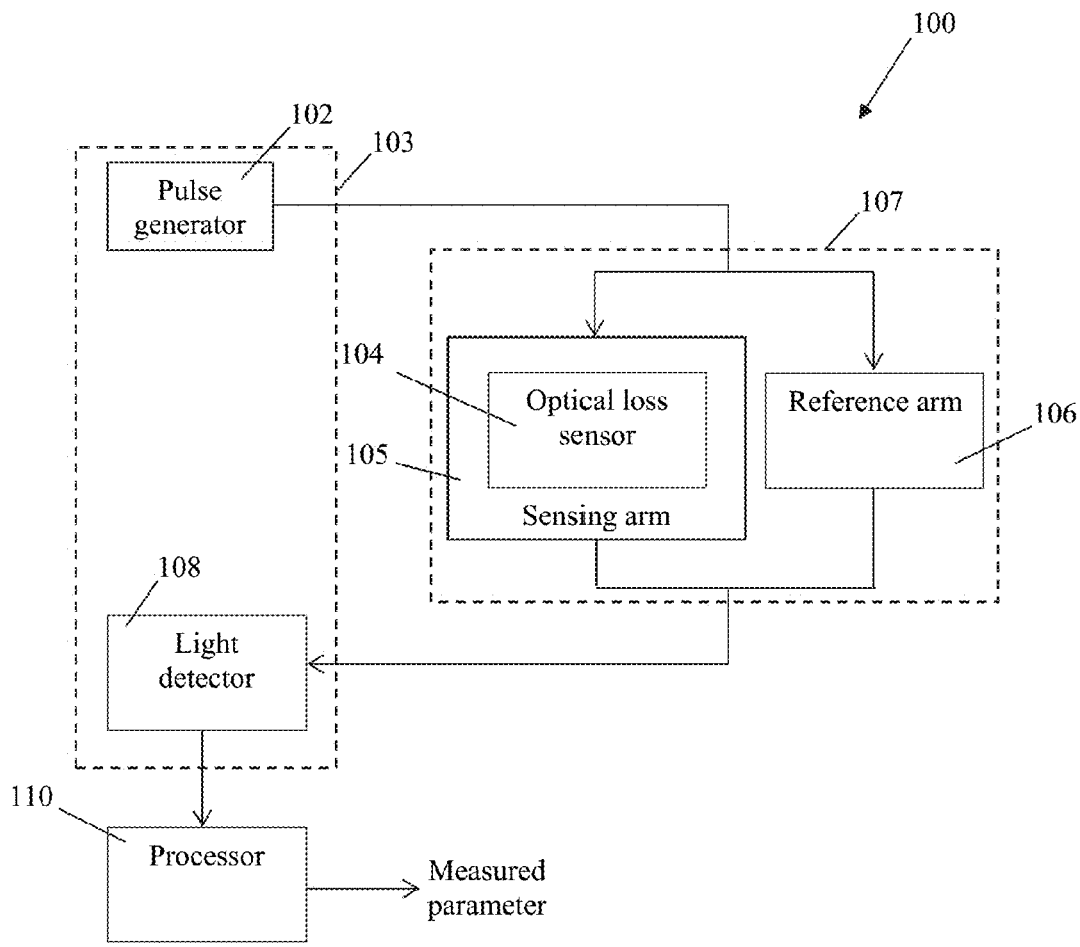
FIG. 1 is a block diagram of an optical system for measuring an environmental parameter, in accordance with an embodiment.

FIG. 1 illustrates one embodiment of an optical system 100 for remotely measuring an environmental parameter. The environmental parameter may be a physical characteristic of a fluid such as a gas or a liquid, a physical characteristic of a solid, etc. The optical system 100 comprises an optical pulse generator 102, a spectral loss ratiometric sensor 104 (hereinafter referred to as a spectro-ratiometric sensor), a sensing arm 105 comprising the spectro-ratiometric sensor 104, a reference arm 106, a light detector 108, and a processor 110. The pulse generator 102 and the light detector 108 form together an interrogator unit 103. The sensing arm 105 comprising the spectro-ratiometric sensor 104 and the reference arm 106 form together a sensing unit 107.

The pulse generator 102 is adapted to emit at least two optical pulses each having a different wavelength. While in the description below it is referred to two light pulses having different wavelengths, it should be understood that the pulse generator 102 may be adapted to generate more than two pulses having different wavelengths.

In one embodiment, the at least two pulses each have a different wavelength comprised in the infrared range such as in the telecommunication bandwidth.

In another embodiment, the at least two pulses each have a different wavelength comprised in the ultraviolet (UV) range, the visible (VIS) range or the near-infrared (NIR) range. The two light pulses may both have a different wavelength contained in the VIS range or the NIR range. In another example, one pulse may have a wavelength contained in the VIS range and the other pulse may have a wavelength contained in the NIR range.

In one embodiment, light contained in the VIS range has a wavelength comprised between about 390 nm and about 700 nm. In one embodiment, light contained in the NIR range has a wavelength comprised between about 700 nm and about 900 nm. In one embodiment, light contained in the UV range has a wavelength comprised between about 200 nm and about 390 nm.

The pulse generator 102 may be adapted to emit substantially concurrently at least two pulses of light each having a different wavelength. Alternatively, the pulse generator 102 may be adapted to successively emit at least two pulses of light each having a different wavelength.

In one embodiment, the pulse generator 102 comprises at least two different light sources each adapted to emit light pulses at a respective wavelength.

In one embodiment, the pulse generator 102 may comprise at least one pulsed light source such as a Q-switched laser. In another embodiment, the pulse generator 102 may comprise at least one light source and at least one optical modulator such as an electro-optic modulator for modulating the light emitted by the light source and generating the light pulses. The pulse generator 102 may also be a laser diode of which the current provided by a power supply is modulated for generating pulses.

The pulse generator 102 is optically connected to the sensing arm 105 which comprises the spectro-ratiometric sensor 104 and to the reference arm 106 so that the generated pulses having different wavelengths be each split into two pulses, i.e. a sensing pulse and a reference pulse for each wavelength. For each wavelength, the sensing pulse propagates through the spectro-ratiometric 104 along the sensing arm 105 while the reference pulse propagates along the reference arm 106. It should be understood that the system 100 comprises any adequate device (not shown) for splitting or dividing each light pulse emitted by the pulse generator 102 into two pulses, such as a beam or pulse splitter, a coupler, or the like. In one embodiment, the sensing pulse and the reference pulse are substantially identical. In this case, a 3 dB coupler may be used for splitting the generated pulse into substantially identical pulses. In another embodiment, the sensing pulse and the reference pulse may be different. For example, the sensing and reference pulses may have different amplitudes.

The spectro-ratiometric sensor 104 is an optical sensor of which the optical absorption spectrum, and/or the optical loss spectrum characteristics change as a function of the environmental factor/parameter to be measured, i.e. a factor or parameter of the environment surrounding the optical loss sensor 104. As a result, the differential loss experienced by at least two optical pulses having different wavelengths and propagating therethrough varies as a function of the environmental parameter value. In order to determine the value of the environmental parameter, the optical spectro-ratiometric sensor 104 requires the use of at least two different wavelengths, i.e. the optical loss at at least two different wavelengths must be known in order to determine the value of the environmental parameter. Therefore, the spectro-ratiometric sensor 104 may also be referred to as a differential loss sensor.

The spectro-ratiometric sensor 104 may be adapted to sense any adequate environmental factor/parameter such as a temperature, a strain, a pressure, an acoustic signal, a molecular concentration, an ion concentration, an acceleration, humidity, a magnetic and/or electric field, an electrical current, a biomarker, a radiation, or the like. As a result, when the value of the environmental parameter varies, the amount of loss experienced by the light pulses propagating through the optical spectro-ratiometric sensor 104 varies. In one embodiment, the optical loss characteristics (comprising absorption) for the optical loss sensor depends on the wavelength of the light pulse. As a result, when the environmental parameter has a given value, the loss of a first light pulse having a first wavelength and propagating through the spectro-ratiometric sensor 104 may be different from the loss experienced by a second pulse having a second and different wavelength. Similarly, when the environmental parameter experiences a given variation, the loss variation for a first light pulse having a first wavelength and propagating through the spectro-ratiometric sensor 104 may be different from the loss variation experienced by a second pulse having a second and different wavelength.

In one embodiment, the spectro-ratiometric sensor 104 uses a dye or a light-absorbing indicator as an indicator of change in the environmental parameter/factor. The light-absorbing indicator could be any adequate compound that changes its optical absorption spectrum under the influence of an environmental parameter/factor. For example, the light-absorbing indicator may comprise adequate quantum dots or polymer semiconductors.

In one embodiment, the spectro-ratiometric sensor 104 directly provides an optical response to a given environmental parameter or mix of parameters. In the case of a chemical spectro-ratiometric sensor, direct sensitivity refers to an indicator which is directly in equilibrium with the analyte, such as a pH sensor or optode.

In another embodiment, the spectro-ratiometric sensor 104 indirectly provides an optical response to a given environmental parameter or mix of parameters. In the case of a chemical spectro-ratiometric sensor, indirect sensitivity in a chemical sensor refers to a chemical equilibrium between the indicator and the analyte which is carried on by many intermediates which are in equilibrium with each other, such as an ion sensor.

In one embodiment, the spectro-ratiometric sensor 104 comprises an optical fiber-based optode which uses a sensing membrane deposited on an adequate substrate exterior to the fiber, on the fiber tip or surrounding the fiber core. When using a membrane as an optical fiber cladding for chemical spectro-ratiometric sensors 104, the analyte may diffuse into the membrane/cladding and a chemical indicator is provided in the cladding for causing a variation of the optical absorption as a function of the chemical species. The cladding is interrogated by the evanescent wave of the guided light in the optical fiber. Analysis of the measured absorption spectra provides an indication of the presence of given chemicals. When using the evanescent wave sensors for other environmental parameters/factors, the variation of the optical absorption of the cladding is function of the environmental parameter/factor. Physical principles that induce changes in an absorption or loss spectrum in a sensing cladding may comprise thermochromism for temperature sensing, solvatochromism for solvent vapor detection, electrochromism for current sensing, ionochromism for ion sensing, halochromism for pH sensing, piezochromism for pressure sensing, and/or the like.

In another embodiment, the spectro-ratiometric sensor 104 comprises an optical fiber-based optode which uses no membranes. In this case, the fiber core or tip is directly in contact with a solution for example.

In one embodiment, the spectro-ratiometric sensor 104 operates only in the UV, VIS and/or NIR range. In this case, the pulse generator 102 is adapted to generate pulses having different wavelengths comprised in the UV, VIS and/or NIR range.

In one embodiment, the reference arm 106 comprises an optical waveguide having a predetermined length. The predetermined length of the reference arm 106 is chosen so as to be different from the length of the sensing arm 105 which comprises the spectro-ratiometric sensor 104. The length difference between the sensing arm 105 and the reference arm 106 is chosen so that, for each wavelength, the sensing pulse and the reference pulse substantially do not overlap in time when reaching the light detector 108.

It should be understood that, for each wavelength, the sensing pulse may experience a different loss with respect to the reference pulse since it propagates through the spectro-ratiometric sensor 104 which induces the different loss according to the value of the sensed environmental parameter. Therefore, the different loss experienced by the sensing pulse relative to the reference pulse is indicative of the value of the environmental parameter, when combined with the loss experienced by the other wavelength pulse(s) relative to their reference pulse(s).

In one embodiment, the length of the sensing arm 105 is greater than that of the reference arm 106. In another embodiment, the length of the sensing arm 105 comprising the spectro-ratiometric sensor 104 is less than that of the reference arm 106.

In one embodiment, an optical delay line is inserted either in the sensing arm 105 or in the reference arm 106 to induce an additional time delay between the sensing pulse and the reference pulse. The optical delay line may be any adequate device adapted to induce a time delay. For example, the optical delay line may be a multipass cell. In another example, the optical delay line may be an optical waveguide such as an optical fiber having a given length chosen to induce an adequate time delay between the sensing pulse and the reference pulse so that they do not overlap in time while reaching the light detector 108.

The sensing arm 105 comprising the spectro-ratiometric sensor 104, and the reference arm 106 are optically connected to the light detector 108 via an optical link or connection so that, for each wavelength, the sensing pulse and the reference pulse may propagate up to the light detector 108. It should be understood that any adequate optical link adapted to propagate optical pulses having the wavelengths generated by the pulse generator 102 may be used. In one embodiment, the optical link is an optical fiber. The optical fiber may be single mode at the wavelengths of the light pulses generated by the pulse generator 102. Alternatively, the optical fiber may be multimode at the wavelengths of the light pulses generated by the pulse generator 102.

In one embodiment, the sensing arm 105 and the reference arm 106 are connected to the optical detector 108 via a same optical waveguide such as an optical fiber. In this case, the optical system 100 further comprises an adequate device for receiving the sensing pulses and the reference pulses from the sensing arm 105 and the reference arm 106, respectively, and propagating the received sensing and reference pulses into the same optical waveguide. For example, the optical system 100 may further comprise an optical beam or pulse combiner, an optical coupler, or the like to propagate the sensing and reference pulses in the same optical waveguide.

The light detector 108 is adapted to detect light having the same wavelengths as the ones of the light pulses emitted by the pulse generator 102, and measure the optical energy of the sensing and reference pulses for each wavelength. While in the present description it is said to be adapted to measure the optical energy of light pulses, it will be clear to those skilled in the art that the light detector 108 may be adapted to measure any physical quantity equivalent to an optical energy such as a number of photons, a pulse amplitude, and/or the like. In one embodiment, the light detector 108 is a photon counting detector. In an embodiment in which a time delay is introduced in the sensing arm 105, the reference pulse is the first pulse to reach the light detector 108. In this case, for each wavelength, the light detector 108 first detects the reference pulse and measures its optical energy. Then, the light detector 108 detects the sensing pulse and measures its respective optical energy. In an embodiment in which the time delay is introduced in the reference arm, the sensing pulse is the first pulse to reach the light detector 108. In this case, for each wavelength, the light detector 108 first detects the sensing pulse and measures its optical energy. Then, the light detector 108 detects the reference pulse and measures its respective optical energy.

The processor 110 is in communication with the light detector 108 in order to receive the measured optical energy for the sensing and reference pulses at each wavelength from the light detector 108. The processor 110 is adapted to determine the value of the sensed environmental parameter using the difference between the optical energy of the detected sensing pulse and that of the detected reference pulse for each wavelength. For each wavelength, the loss experienced by the sensing pulse while propagating in the spectro-ratiometric sensor 104 is determined using the optical energy of the sensing and reference pulses. In one embodiment, the loss experienced by the reference pulse or the sensing pulse in the optical delay line is neglected. In another embodiment, the loss experienced by the sensing pulse while propagating in the optical loss sensor 104 is obtained while further taking into account the optical loss experienced by the sensing pulse or the reference pulse while propagating in the optical delay line.

In one embodiment, once the optical system 100 has been assembled, the resulting assembly consisting of the reference arm, the sensing arm and/or any additional components such as a pulse combiner and a pulse splitter is calibrated by exposing the spectro-ratiometric sensor 104 to environments of known values of the environmental factor/parameter. For each environment of known value, the optical energies of the sensing and reference pulses are recorded for all of the at least two measurement wavelengths to be generated by the pulse generator. Other values may be recorded, such as the ratio of the sensing arm's pulse energy over the reference arm's pulse energy at all of the at least two measurement wavelengths and the like. In another embodiment and more generally, the pulse energy from the sensing arm 105 and the pulse energy from the reference arm 106 are measured and recorded at a number of wavelengths, not only the at least two wavelengths to be generated by the pulse generator 102 of the system 100, and are measured and recorded for all of the environments of known values of the environmental factor/parameter at the aforementioned number of wavelengths. This data is to become the input to an algorithm along with the recorded pulse energy from the sensing arm 105 and the recorded pulse energy from the reference arm 106 at all of the at least two wavelengths of the measurement system 100 to determine the value of the unknown environmental factor/parameter. In one embodiment, it may be preferable that the calibration hardware be the same as the measurement system to be deployed. In another embodiment, they may be different. The ensemble could also be calibrated before deployment with respect to temperature for example. The output from this calibration step could then also become an input to the measurement algorithm, or a look up table could then be used if the temperature is known somehow. In one embodiment, the assembly is designed to be independent of any parameter except, eventually, wavelength (which is known). The algorithms could, for example, take into account that in the sensing arm 105, there are other losses to account for besides the loss in the spectro-ratiometric sensor 104. There is, for example, coupling losses into and out of the spectro-ratiometric sensor 104. Losses occurring in the sensing arm 105 may also be considered. There could be other optical elements that generate coupling losses and/or propagation losses. All of these losses should have a linear relationship with the input pulse energy to the sensing arm 105. The loss due to absorption or otherwise in the spectro-ratiometric sensor 104 itself due to the environmental factor/parameter can be determined if the losses that are not due to the environmental factor/parameter are calibrated with respect to wavelength and other parameters or engineered to be independent of any other factor other than absorption/loss in the spectro-ratiometric sensor.

In one embodiment, the optical system 100 comprises at least one optical link or waveguide for optically connecting the pulse generator 102 to the sensing unit 107, and the sensing unit 107 to the light detector 108, the length of said optical link being such that the optical signal propagating from the generator 102 to the sensing unit 107 and then to the light detector 108 suffers high loss or high differential loss. The length of the optical connection is such that, for the wavelengths contained in the VIS range and/or the NIR range, the generated pulses that become the sensing and reference pulses experience high loss or high differential loss while propagating along the optical link. For example, the high loss or high differential loss optical connection may comprise at least one optical fiber having a given length presenting high loss for wavelengths comprised in the VIS range and/or NIR range. In one embodiment, high loss corresponds to a loss that would bring to detected signal within about 20 dB of the system's optical detection limit.

In one embodiment, the optical system 100 operates in transmission so that the sensing pulse at each wavelength makes only one pass through the spectro-ratiometric sensor 104. In one embodiment, a first optical waveguide optically connects the pulse generator 102 to the sensing unit 107, and a second and different optical waveguide optically connects the sensing unit 107 to the light detector 108. A first optical coupler may be used at the output of the first optical waveguide to split the incoming pulses generated by the pulse generator 102 into sensing pulses and reference pulses. A second optical coupler may be used for collecting the sensing pulses coming from the spectro-ratiometric sensor 104 and the reference pulses coming from the reference arm 106 and coupling them into the second optical waveguide. In another embodiment, a same optical waveguide optically connects both the pulse generator 102 and the light detector 108 on one end to the spectro-ratiometric sensor 104 and the reference arm 106 on the other end. In this case, a first circulator may be used for optically connecting together the pulse generator 102, the light detector 108, and the input of the single optical waveguide so that a pulse generated by the pulse generator 102 be propagated in the optical waveguide and a pulse coming from the optical waveguide be transmitted to the light detector 108. A second circulator may be used for optically connecting together the output of the optical waveguide, the sensing arm 105, and the reference arm 106. A first coupler may connect one output of the circulator to the sensing and reference arms 105 and 106 so that a pulse coming from the optical waveguide be split into a sensing pulse to be propagated in the sensing arm 105 and a reference pulse to be propagated into the reference arm 106. A second coupler may connect an input of the circulator to the outputs of the sensing and reference arms 105 and 106 so that the sensing pulse coming from the spectro-ratiometric sensor 104 and the reference pulse coming from the reference arm 106 be coupled into the optical waveguide.

In another embodiment, the optical system 100 operates in reflection. In this case, the sensing and reference arms 105 and 106 each comprise a light reflector at the end thereof for reflecting the sensing and reference pulses, respectively. It should be understood that any adequate light reflector adapted to reflect a light pulse may be used. For example, a straight cleaved fiber end coated with aluminum may be used. In one embodiment, a single and same optical waveguide optically connects the optical pulse generator 102 and the light detector 108 on one end to the sensing and reference arms 105 and 106 on the other end. As described above, a circulator may be used to optically connect together the pulse generator 102, the light detector 108, and the input of the generator 102, the light detector 108, and the input of the optical waveguide. A coupler optically connects together the output of the optical waveguide, the sensing arm 105 so that a pulse coming from the optical waveguide be split into the sensing pulse and the reference pulse, and the sensing and reference pulses reflected by the optical reflectors be combined into the optical waveguide.

In another embodiment, two different optical waveguides may be used for optically connecting the pulse generator 102, the light detector 108, the sensing arm 105, and the reference arm 106. A first end of a first optical waveguide is connected to the pulse generator 102 and the second end of the first optical waveguide is connected to a circulator. A first output of the circulator is connected to a coupler for splitting a pulse coming from the first optical waveguide into a sensing pulse to be propagated in the sensing arm 105 and a reference pulse to be propagated in the reference arm 105. The sensing and reference pulses are each reflected by their respective optical reflector and propagates back to the splitter/coupler and then to the circulator. The sensing and reference pulses exit the circulator by a second output which is optically connected to the second optical waveguide. The other end of the second optical waveguide is connected to the optical detector 108 so that the reflected sensing and reference pulses be detected by the light detector 108. In a further embodiment, the circulator may be omitted and a coupler may be used for connecting together the first and second optical waveguides and the sensing and reference arms 105 and 106.

In one embodiment, the light detector 108 comprises at least two photodetectors each adapted to detect light having a wavelength corresponding to that of a respective pulse generated by the pulse generator 102. In this case, the system may further comprise a wavelength-division multiplexing (WDM) coupler for coupling the sensing and reference pulses having a first wavelength to a first photodetector adapted to detect light having the first wavelength, and coupling the sensing and reference pulses having a second wavelength to a second photodetector adapted to detect light having the second wavelength. In another embodiment, a power divider coupler may be used to split each pulse coming from the sensing unit into two pulses. A respective bandpass filter is located at each output of the power divider coupler. The bandpass filter positioned between a first output of the power divider coupler and the photodetector adapted to detect light having the first wavelength is adapted to allow pulses having the first wavelength to propagate therethrough while preventing the propagation of pulses having the second wavelength. The bandpass filter positioned between the second output of the power divider coupler and the photodetector adapted to detect light having the second wavelength is adapted to allow pulses having the second wavelength to propagate therethrough while preventing the propagation of pulses having the first wavelength. The power divider coupler may be a 3 dB coupler for example.

In one embodiment, the light detector 108 comprises a photon counting detector adapted to measure photon numbers. In this case, the optical system 100 may comprise a controller operatively connected to the pulse generator 102 and the photon counting detector. The controller may be adapted to control the pulse generator 102 to trigger the generation of pulses and the photon counting detector. Knowing the time at which a pulse has been generated by the pulse generator 102, the controller may determine time windows during which the sensing pulse and the reference pulse will be received by the photon counting detector using the characteristics of the components of the optical system 100 such as the propagation time of the pulses, the time delay experienced by the sensing pulse or the reference pulse, etc. The controller may activate the photon counting detector only during the determined time windows.

The optical system 100 may be referred to as a differential optical loss sensing system since it uses at least two different wavelengths for measuring the value of an environmental parameter through the change in the absorption or loss spectrum of an optical loss sensor.

In one embodiment, the spectro-ratiometric sensor 104 is an ion or molecular concentration sensor that may come in the form of a fiber optic sensor of which the shape of the optical absorption spectrum or loss spectrum changes with the ion or molecular concentration in a fluid surrounding the fiber optic sensor. The optical loss of optical signals having at least two different wavelengths is measured in order to determine the change in the absorption/loss spectrum and subsequently the ion or molecular concentration.

In one embodiment and in order to transmit light over very great fiber lengths, light of wavelength in the range of 900 to 1900 nm is usually used, along with low-OH fibers. Particularly, the telecommunication band around 1550 nm is usually used. Interrogating a sensor at the end of a very long fiber link, such as tens of kilometers, is thus usually done in the low fiber loss spectral range, and particularly in the telecommunication band. On the other hand, some optical loss sensors only operate in the VIS or NIR range. These sensors are not considered in systems requiring long optical link(s) which therefore present(s) high optical loss, such as multiple kilometers of optical fiber, since measuring the loss in the sensing element of such a sensor is usually considered impractical or unreliable because of high loss and/or high differential loss in the fiber link(s).

Figure 2:
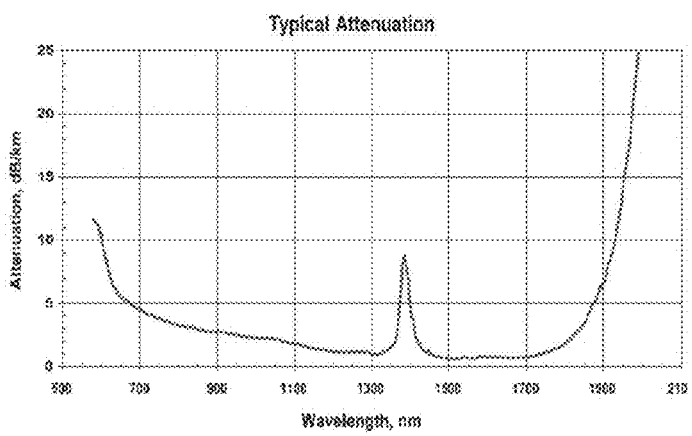
FIG. 2 is a graph illustrating the attenuation of an optical fiber as a function of wavelength, in accordance with the prior art.

When looking at loss curves for multimode fiber products from Fiberguide™, Polymicro™, CeramOptec™ or the like, an example of which is presented in FIG. 2, the minimum loss is less than 1 dB/km and starts to rise significantly at 900 nm, where losses are greater than about 3 dB/km. Each 1 dB/km of additional loss adds a factor of about 10 in loss over about 10 km of total fiber travel or a factor of about 100 for a 10-km link traveled in both directions, for about 20 km of total travel. In addition, what is measured is a change in the optical absorption/loss spectrum shape, where the difference in losses measured at two or more optical wavelengths is the parameter of interest. When the fiber link losses vary by about 3 or about 4 dB/km between two measurement wavelengths (such as between 550 and 600 nm as illustrated in FIG. 2), and for measurements over fiber links of about 10 km for example, small perturbations in the fiber link loss at any of the measurement wavelengths may greatly affect the measurement accuracy. A pulse energy reference is thus needed.

In one embodiment, multimode fibers are used as they can accept much larger pulse energies than single mode fibers, especially in the visible or near infrared where single mode fiber cores are usually less than 5 μm in diameter whereas multimode fibers can have cores of hundreds of microns in diameter. In consequence, multimode fibers allow longer fiber links because the input energies can be higher.

In one embodiment, photon counting detection is used in order to keep the input light energy per pulse as low as possible not to damage the fiber or generate adverse loss generating non-linear effects therein.

While the above description refers to the use of the system 100 in the context of high loss optical links, it should be understood that the system 100 may also be used in a context in which optical links do not present high losses. For example, the pulse generator 102 may be adapted to generate pulses having a wavelength contained in the long haul telecommunications bandwidth such as around 1550 nm.

In the following, exemplary implementations of the optical system 100 are presented.

Figure 3:
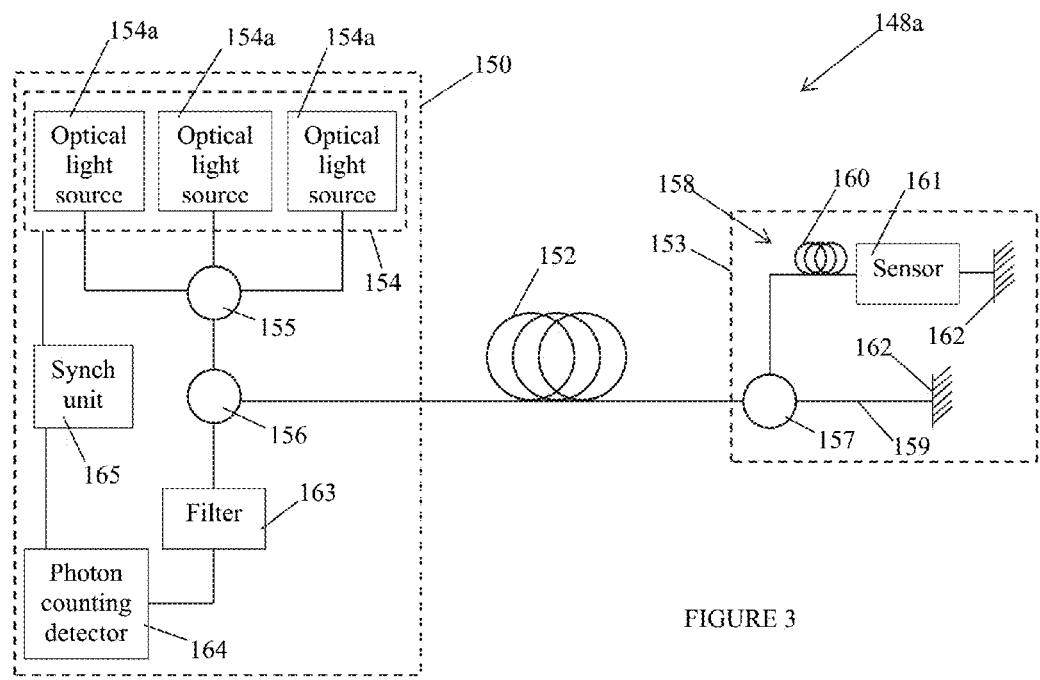
FIG. 3 illustrates an optical measurement system operating in reflection and comprising a single optical link, in accordance with an embodiment.

The optical system 148a illustrated in FIG. 3 comprises an interrogator unit 150, an optical fiber 152, and a sensing unit 153 at the sensor end of the optical fiber 152. The sensing unit 153 comprises a sensing arm 158 which comprises a sensing element or optical loss sensor 161, a delay line 160, and a reflector 162, and a reference arm 159 which comprises an optical waveguide having a predetermined length and a reflector 162. The interrogator unit 150 houses one or multiple optical sources 154 such as lasers. In one embodiment, the interrogator unit 150 comprises three lasers 154a, all having a different emission wavelength, for measuring the difference in optical loss between these wavelengths in the optical loss sensor or sensing element 161 of the sensing unit 153. The lasers may be broad area semiconductor lasers for which the injection current is pulsed and emitting optical pulses of suitable energy. The pulse generator could also be a single laser emitting multiple wavelengths, such as a multi-wavelength dye laser or multi-wavelength optical parametric oscillator. The pulse generator may also be the second harmonic of a Q-switched Nd:YAG laser or pulsed Yb fiber laser or of any other adequate solid state laser. The pulse generator could also be a broadband emitting coherent source of light, covering about 50 nm full width at half maximum for example or engineered to emit light having an optimized spectral shape. The lasers may be pulsed simultaneously and coupled to a single fiber using dichroic filters (bulk or fibered) or beam splitters (bulk or fiber couplers) 155. The lasers could also be pulsed consecutively, one after the other, and coupled to a single fiber using dichroic filters (bulk or fibered) or beam splitters (bulk or fiber couplers) 155. Their pulses may pass through a switch to go from one wavelength to the other. The pulses emitted from fibered optical sources are routed to a fiber optic coupler or circulator (bulk or fibered) 156 and transmitted to the fiber 152. The optical pulse is modified while traveling along the fiber 152. It loses energy because of loss while traveling along the fiber and its temporal shape changes because of optical dispersion, either chromatic or modal.

In one embodiment, optical fibers in the optical fiber links have a spectral attenuation curve, such as that shown in FIG. 2. FIG. 2 shows the attenuation curve for the Ultra Low-OH fiber from Polymicro™. In one embodiment, the range of operation is close to the minimum in attenuation, essentially between the wavelengths 1000 and 1700 nm. For long fiber links, 20 km for example (10 km for getting to the sensor and 10 km return towards the interrogator), the total loss in the optical link using the minimum attenuation of 1 dB/km is 20 dB or a signal 100 times less intense after 20 km of travel than the signal inputted at beginning of the optical fiber link. In the visible wavelengths range, essentially between about 390 and about 700 nm, losses are much higher. With a loss of 11 dB/km at about 600 nm, the total loss would be 220 dB for the same 20 km of fiber travel. That is $10^{22}$ less optical intensity at the output than at the input. Not only the total loss is very important, but the differential loss between any two wavelengths could also be very important. A 1 dB/km difference between two wavelengths adds up to one wavelength having 100 times more loss than the other at the end of the fiber travel. As can be seen from the attenuation curve, this could easily happen in the visible range.

Figure 6:
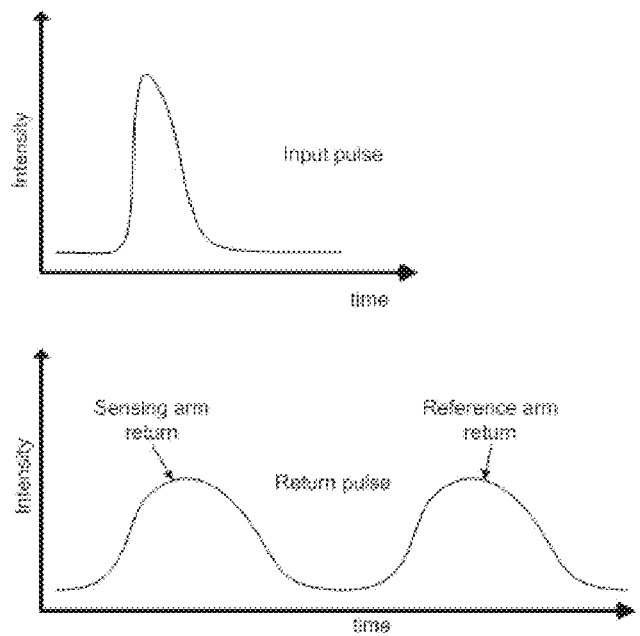
FIG. 6 illustrates the temporal profiles of an input pulse, a sensing pulse, and of a reference pulse, in accordance with an embodiment.
Figure 8:
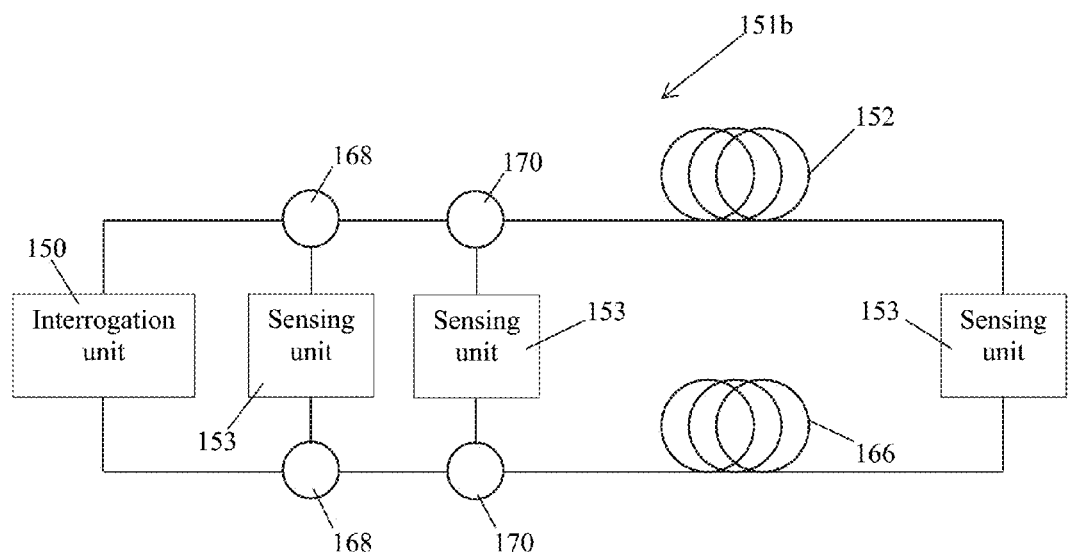
FIG. 8 illustrates an optical measurement system comprising three optical loss sensors connected along two optical links, in accordance with an embodiment.

The optical pulse is split into a sensing arm 158 and a reference arm 159 when going through a fiber optic coupler or bulk beam splitter 157. The sensing arm 158 is comprised of an optical delay line 160, made of a piece fiber having a predetermined length for example, a spectro-ratiometric sensor 161 and a reflector 162. The sensing arm 158 is longer than the reference arm 159 in order for the return to be comprised of two distinct optical pulses as illustrated in FIG. 6. The difference in fiber length is predetermined so that the sensing and reference pulses do not overlap in time when reaching the detector 164. The opposite is also possible, namely a sensing arm 158 shorter than the reference arm 159. There is loss in the sensing arm that does not occur in the reference arm 159, owing to the specific function of the optical spectro-ratiometric sensor 161. The reference arm 159 is needed because of probable time varying losses along the fiber that need to be eliminated from the measurement.

In an embodiment in which it is adapted to measure an ion concentration, the spectro-ratiometric sensor 161 can be an optical fiber core surrounded by a special membrane that may contain chromoionophores. When the membrane is in contact with a fluid containing the ions to be detected (such as $Na^+$, $Ca^{2+}$, $K^+$, $Cl^-$, or the like), the shape of the absorption spectrum of the membrane changes, depending on the ion concentration. The light enters the fiber core of the sensor 161 and interacts with the membrane through evanescent waves. The shape of the optical transmission spectrum in the spectro-ratiometric sensor 161 changes with ion concentration and this change in transmission, caused by the change in the shape of the absorption spectrum of the membrane, is measured by the interrogator unit 150. This type of sensor can also be engineered to detect neutral species, in fluids or in gaseous form. It can also be engineered to detect other physical parameters, such as pH. In one embodiment, the spectro-ratiometric sensor 161 comprises a pair of optical collimators mounted face to face in an appropriate mechanical housing, and a filtered gas or fluid flows freely between the collimator pairs. In another embodiment, the spectro-ratiometric sensor 161 comprises an optical collimator-reflector pair for the same use. It should be understood by those skilled in the art that the spectro-ratiometric sensor 161 may take on a large variety of configurations.

Reflecting surfaces 162 are positioned at the end of each arm 158, 159, and the optical sensing and reference pulses are returned and coupled back to the fiber 152 through coupler 157. The pulsing of the optical sources 154a is for discriminating between the return from the sensing arm 158 and the return from the reference arm 159, and also to discriminate against other scattering processes such as Rayleigh or Raman backscattering. The return pulses travel along the fiber to the coupler/circulator 156 and are directed to an optical filtering unit 163 that separates the returns from the different lasers 154a, when they are simultaneous, and filters them from other in-fiber parasitic processes generated at other wavelengths, then to the detector and ancillary counting electronics 164.

In one embodiment and in order to have the desired signal in a reasonable time, such as in order to have a given signal to noise ratio within a given measurement time, per measurement wavelength, a relatively high energy pulse is outputted from the generator and inputted to the optical fiber link for the most absorbed optical signal. The input light energy per pulse is kept as low as possible not to damage the fiber or induce adverse non-linear effects therein. These thresholds for damage and non-linear effects, along with optical noise sources such as thermal photons, determine the maximum loss or fiber link length that the measurement can support in order to have a specified signal to noise ratio within an imposed measurement time. This input light energy for this maximum length is such that only a few photons per pulse fall onto the detector. It may also happen that less than one photon per pulse falls onto the detector. In these cases, photon counting is used in order to detect an optical signal. This is possible when there are no other sources of optical energy at the wavelengths of measurement other than a few thermal photons. In one embodiment, the photon counting detector is a photomultiplier tube. The photon counting detector may also be a silicon avalanche photodiode in Geiger mode or a so-called solid state photomultiplier, which is an array of silicon avalanche photodiodes in Geiger mode. In another embodiment, the photon counting detector may be a gated photon counting detector in which only the photons received during a temporal counting gate or time window corresponding to one or the other of the return pulses are counted. The use of two counting gates may be preferable, one for the sensing pulse and one for the reference pulse. It may also be possible to do time correlated photon counting inside a single wide temporal gate that encompasses both returns. It will be clear for those skilled in the art that there could be an analog detection part to supplement the photon counting part in order to optimize the dynamic range of the detection. The timing of the counting gates with respect to the input laser pulses is controlled by the synchronization and gating electronics 165.

Figure 4:
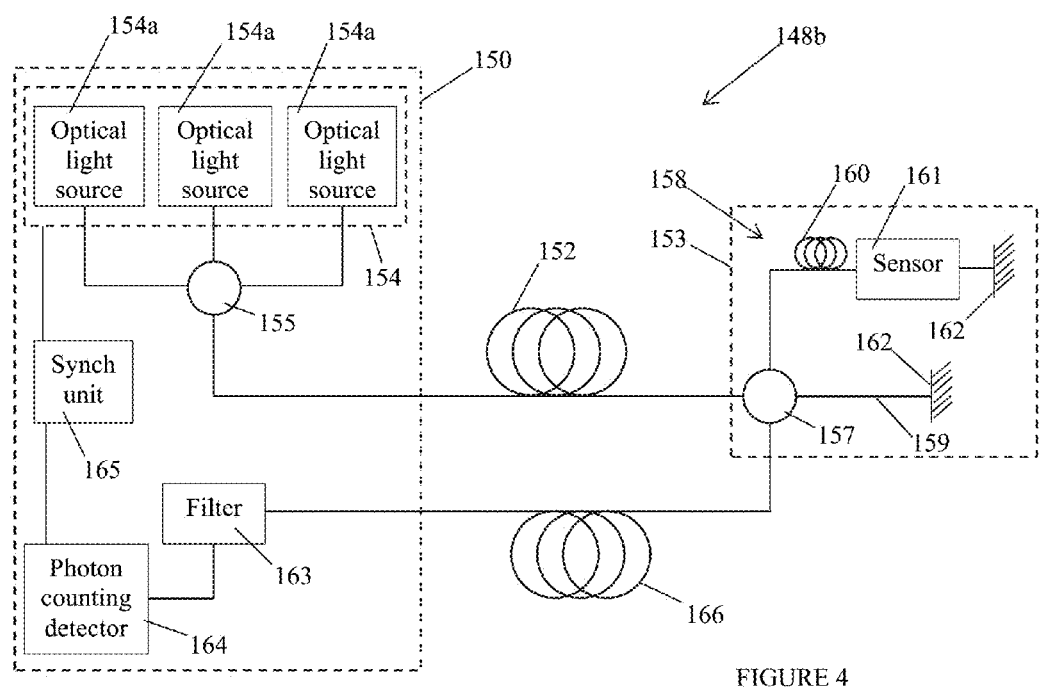
FIG. 4 illustrates an optical measurement system operating in reflection and comprising two single optical links, in accordance with an embodiment.
Figure 5:
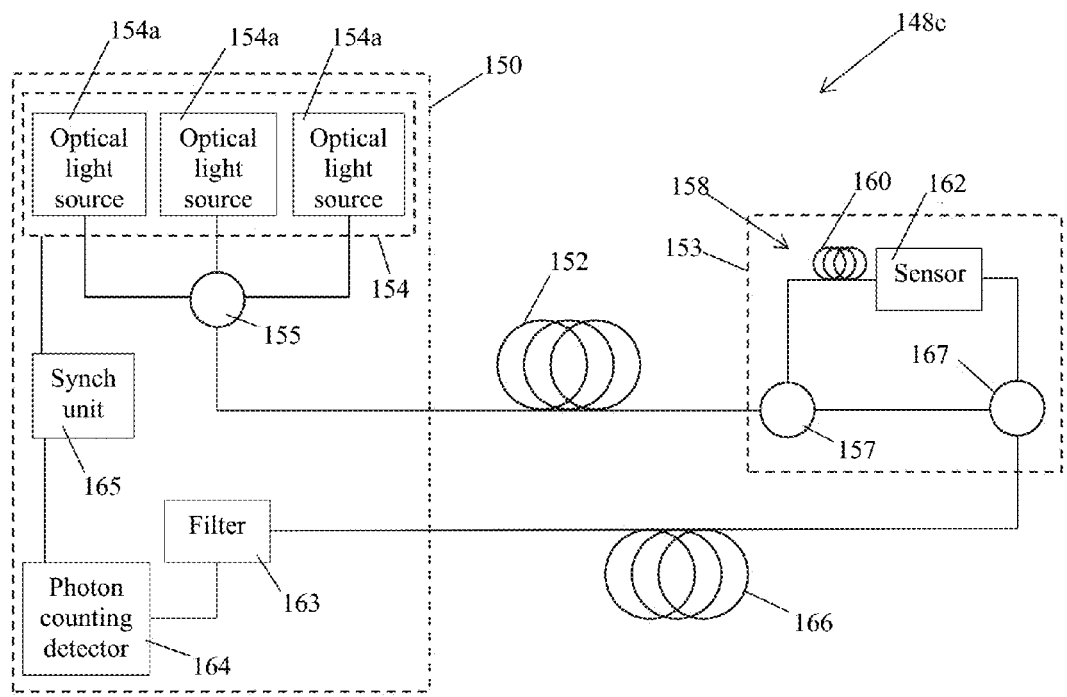
FIG. 5 illustrates an optical measurement system operating in transmission and comprising two optical links, in accordance with an embodiment.

The return fiber can be a different fiber 166 as illustrated in FIG. 4 which illustrates an optical measurement system 148b operating in reflection, or the same fiber 152 as illustrated in FIG. 3. The reflecting surfaces 162 could be replaced by an output coupler 167 connected to the return fiber 166 as illustrated in FIG. 5 which illustrates an optical measurement system 148c operating in transmission. When using distinct fibers for channeling the incoming and outgoing pulses, Rayleigh and other backscattering are no longer a concern.

In reflection mode with a single fiber 152, the pulse repetition rate is limited by the round-trip time in the fiber. This is because of parasitic effects such as Rayleigh backscattering. The Rayleigh backscattering of one pulse must not overlap, at least significantly, with the sensor return of another pulse. In embodiments in which a second fiber is used for propagating the sensing and reference pulses, this is not the case, and the pulse repetition rate can be higher and is limited only by the pulse stretching caused by the dispersion effects. This allows for lower input pulse energies.

In one embodiment, the length of the fiber delay 160 essentially depends on modal dispersion when the optical fibers 152, 166 are multimode, and thus on fiber numerical aperture. The lower numerical apertures reduce modal dispersion and delay length, but using such fibers may not always be possible and depends on coupling losses to the spectro-ratiometric sensor 161.

Figure 7:
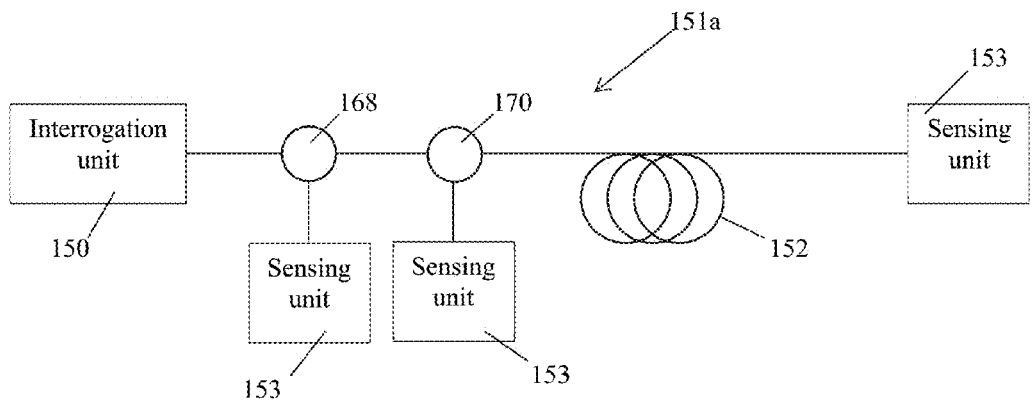
FIG. 7 illustrates an optical measurement system comprising three optical loss sensors connected along a single optical link, in accordance with an embodiment.

In one embodiment, the optical system comprises more than one sensing unit 153. Operating multiple loss sensors on a single fiber optic link may be a requirement in some particular applications. This multiplexing of sensing units could be done in multiple ways such as wavelength division multiplexing or time domain multiplexing. In some cases, the optical signals pass through the sensing unit and continue to travel towards the next sensing unit whereas in other cases light is coupled out of the main fiber line, such as in the optical measurement system 151a illustrated in FIG. 7. The most straightforward coupling scheme is usually to have couplers 168 and 170 presenting the same coupling ratio on all sensing units, for example a 50/50 ratio (or 3 dB coupler). But in the case of a high loss fiber link this would require having a huge dynamic range at the detector end. When the first sensing unit is close to the interrogator unit and is generating much more signal than a sensing unit at the end of the fiber link and at the end of much more fiber loss, the number of sensing units that could be multiplexed on the fiber link for a given minimum signal to noise ratio and measurement time would reduce. For these reasons, the preferred embodiment for multiplexing would be to have a coupling ratio dependent on the distance to the interrogator unit and on the number of multiplexed sensing unit as illustrated in FIG. 7. The closer sensing unit 153 may have a very low coupling to the main fiber link, such as a ratio of 1 part out of a thousand to the sensing unit (1:999), whereas the last sensing unit would be directly on the fiber line 152. The second sensing 153 unit may have a coupling ratio of 1:99 for example. The sensing units 153 may be of the same type. The number of sensing units 153 comprised in the optical system may vary. For example, the optical system may comprise tens of sensing units 153. The coupling ratios are optimized for maximum signal to noise ratios and minimum dynamic range.

In the single fiber link scheme illustrated in FIG. 7 above, light traveling towards the next sensing units 153 interferes with the return from the previous sensing unit 153. The Rayleigh backscattering of the pulse traveling towards a given sensing unit 153 will interfere with the measurement of the previous sensing unit 153 in this approach. In one embodiment, the signal traveling towards a given sensing unit 153 is very strong compared to the signal coupled to the previous sensing unit 153 and returned towards the interrogation unit 150. So even though Rayleigh backscattering is weak, it could interfere with the reading of the previous sensing unit 153 when the coupling ratio to sensing unit 153 is very small. It would thus be preferable to have an incoming fiber and an outgoing fiber, thus a two fiber optical measurement system 151b as illustrated in FIG. 8. Couplers 168 and 170 couple out of the fiber and into the fiber respectively with the same ratios. The same applies for the couplers to the other sensing units 153 along the fiber link.

The embodiments of the invention described above are intended to be exemplary only. The scope of the invention is therefore intended to be limited solely by the scope of the appended claims.

I claim:

1. An optical system for sensing an environmental parameter, comprising:
   an optical pulse generator for generating a first pulse having a first wavelength and a second pulse having a second and different wavelength;
   a pulse splitter for splitting each one of the first and second pulse into a sensing pulse and a reference pulse;
   a sensing arm connected to the pulse splitter for receiving the sensing pulses therefrom, the sensing arm comprising a spectro-ratiometric sensor for sensing the environmental parameter;
   a reference arm connected to the pulse splitter for receiving the reference pulses therefrom;
   a time delay line contained in one of the sensing arm and the reference arm, the time delay line for delaying a propagation of one of the sensing pulses and the reference pulses relative to a propagation of another one of the sensing pulses and the reference pulses;
   a light detector for detecting the sensing pulse and the reference pulse and measuring an optical energy of the sensing pulse and the reference pulse, for the first and second wavelengths; and
   at least one optical link for optically connecting the pulse generator to the pulse splitter, and the sensing and reference arms to the light detector.

2. The optical system of claim 1, wherein the light detector comprises a photon counting detector.

3. The optical system of claim 2, wherein the photon counting detector comprises a gated photon counting detector.

4. The optical system of claim 1, wherein the at least one optical link comprises a single optical link.

5. The optical system of claim 1, wherein the at least one optical link comprises a first optical link for optically connecting the pulse generator to the pulse splitter, and a second optical link for optically connecting the sensing and reference arms to the light detector.

6. The optical system of claim 1, wherein the sensing and reference arms each further comprise a light reflector for reflecting the sensing pulses and the reference pulses, respectively.

7. The optical system of claim 1, wherein the at least one optical link comprises at least one optical fiber.

8. The optical system of claim 7, wherein the at least one optical fiber comprises at least one multimode fiber.

9. The optical system of claim 1, further comprising a processor for determining a value of the environmental parameter using the measured optical energy for the sensing and reference pulses.

10. The optical system of claim 1, wherein the spectro-ratiometric sensor comprises an optical fiber-based optode comprising a sensing membrane, the sensing membrane comprising a chemical indicator causing a variation of the optical absorption as a function of the environmental parameter.

11. An optical system for sensing an environmental parameter, comprising:
    an optical pulse generator for generating a first pulse having a first wavelength and a second pulse having a second and different wavelength;
    a plurality of sensing units for sensing the environmental parameter, each comprising:
       a pulse splitter for splitting each one of the first and second pulse into a sensing pulse and a reference pulse;
       a sensing arm connected to the pulse splitter for receiving the sensing pulse therefrom, the sensing arm comprising a spectro-ratiometric sensor for sensing the environmental parameter;
       a reference arm connected to the pulse splitter for receiving the reference pulse therefrom; and
       a time delay line contained in one of the sensing arm and the reference arm, the time delay line for delaying a propagation of one of the sensing pulse and the reference pulse relative to a propagation of another one of the sensing pulse and the reference pulse;
    a light detector for detecting the sensing pulse and the reference pulse from each sensing unit and measuring an optical energy of the sensing pulses and the reference pulses from each sensing unit, for the first and second wavelengths; and
    at least one optical link for optically connecting the pulse generator to the pulse splitters, and the sensing and reference arms to the light detector.

12. A method for remotely sensing an environmental parameter, comprising:
    generating a first pulse having a first wavelength and a second pulse having a second and different wavelength;
    propagating the first and second pulses along at least one optical link;
    splitting each one of the first and second pulse into a sensing pulse and a reference pulse;
    propagating the sensing pulses in a sensing arm, the sensing arm comprising an spectro-ratiometric sensor, thereby sensing the environmental parameter;
    propagating the reference pulses in a reference arm;
    delaying a propagation of one of the sensing pulses and the reference pulses relative to a propagation of another one of the sensing pulses and the reference pulses;
    propagating the sensing pulses and the reference pulses in the at least one optical link; and
    measuring an optical energy of the sensing pulse and the reference pulse, for each one of the first and second wavelengths.

13. The method of claim 12, wherein said propagating the first and second pulses along at least one optical link comprises propagating the first and second pulses along a first optical link, and said propagating the sensing pulses and the reference pulses in the at least one optical link comprises propagating the sensing pulses and the reference pulses in a second and different optical link.

14. The method of claim 12, wherein said propagating the first and second pulses along at least one optical link comprises propagating the first and second pulses along a single optical link, and said propagating the sensing pulses and the reference pulses in the at least one optical link comprises propagating the sensing pulses and the reference pulses in the single optical link.

15. The method of claim 12, wherein said propagating the first and second pulses along at least one optical link comprises propagating the first and second pulses along at least one optical fiber.

16. The method of claim 12, wherein the at least one optical fiber comprises at least one multimode fiber.

17. The method of claim 12, further comprising determining a value of the environmental parameter using the measured optical energy for the sensing and reference pulses.

18. The method of claim 12, wherein said propagating the sensing pulses in a sensing arm comprises reflecting the sensing pulses at an end of the sensing arm, and said propagating the reference pulses in a reference arm comprises reflecting the reference pulses at an end of the reference arm.

19. The method of claim 12, wherein said measuring an optical energy comprises counting a number of photons for each one of the sensing pulse and the reference pulse, for each one of the first and second wavelengths.

20. The method of claim 12, wherein the spectro-ratiometric sensor comprises an optical fiber-based optode comprising a sensing membrane, the sensing membrane comprising a chemical indicator causing a variation of the optical absorption as a function of the environmental parameter.

* * * * *